United States Patent [19]

Osakabe et al.

[11] Patent Number: 5,032,614
[45] Date of Patent: Jul. 16, 1991

[54] SEROTONIN ANTAGONIST

[75] Inventors: Masanori Osakabe, Kawasaki; Hiroto Hara, Machida; Yoshikuni Tamao, Machida; Ryoji Kikumoto, Machida, all of Japan

[73] Assignee: Mitsubishi Kasei Corporation, Tokyo, Japan

[21] Appl. No.: 524,983

[22] Filed: May 18, 1990

[30] Foreign Application Priority Data

May 18, 1989 [JP] Japan .................................. 1-125055

[51] Int. Cl.$^5$ .......................................... A61K 31/195
[52] U.S. Cl. .................................................... 514/561
[58] Field of Search .......................................... 514/561

[56] References Cited

U.S. PATENT DOCUMENTS

| 4,220,603 | 9/1980 | Kikumoto et al. | 562/471 |
| 4,323,568 | 4/1982 | Kikumoto et al. | 562/471 |
| 4,485,258 | 11/1984 | Kikumoto et al. | 562/471 |
| 4,599,419 | 7/1986 | Kikumoto et al. | 562/471 |

Primary Examiner—Stanley J. Friedman
Attorney, Agent, or Firm—Wegner, Cantor, Mueller & Player

[57] ABSTRACT

A method of suppressing vasoconstriction in a warm-blooded animal which comprises administering to said warm-blooded animal an effective amount of a serotonin antagonist compound of the formula (I):

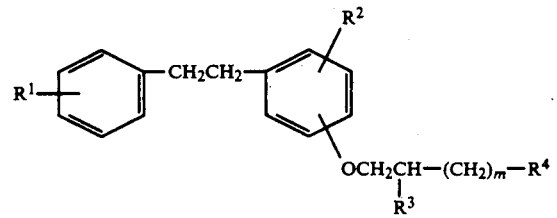

wherein:
$R^1$ is hydrogen, halo, $C_1$-$C_5$ alkoxy or $C_2$-$C_6$ dialkyl amino;
$R^2$ is hydrogen, halo or $C_1$-$C_5$ alkoxy;
$R^3$ is hydrogen, hydroxy, —O—$(CH_2)_n$—COOH or —O—CO—$(CH_2)_l$—COOH, wherein n is an integer of 1-5, and l is an integer of 1-3;
$R^4$ is

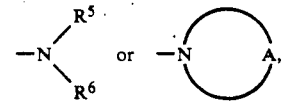

wherein $R^5$ and $R^6$ are each independently hydrogen or $C_1$-$C_8$ alkyl, and A is $C_3$-$C_5$ alkylene or $C_3$-$C_5$ alkylene substituted with carboxy; and
m is an integer of 0-5, or a pharmaceutically acceptable salt thereof. The use of the compound (I) for the preparation of a pharmaceutical formulation useful as a serotonin antagonist is also provided.

4 Claims, No Drawings

SEROTONIN ANTAGONIST

The present invention relates to a new therapeutical use of known compounds. More particularly, it relates to a method of suppressing vasoconstriction by the use of the known compounds. It also relates to the use of the known compounds for the preparation of a pharmaceutical composition useful as a serotonin antagonist.

The present inventors previously discovered that a class of aminoalkoxybibenzyls were useful as a platelet aggregation inhibiting agent (U.S. Pat. No. 4,485,258 corresponding to Japanese Patent Publication (Kokoku) No. 63-13427; 4,599,419 corresponding to Japanese Patent Publication (Kokoku) No. 63-13427; U.S. Pat. No. 4,220,603 corresponding to Japanese Patent Publication (Kokoku) Nos. 60-21578, 61-21463 and 63-10683; and U.S. Pat. No. 4,323,568 corresponding to Japanese Patent Publication (Kokoku) Nos. 60-21578, 61-21463 and 63-10683). Further study on the aminoalkoxybibenzyls has now revealed that part of the aminoalkoxybibenzyls are also useful as a serotonin antagonist.

It has long been known that serotonin plays an important role in the generation and maintenance of the microcirculation disorders associated with platelet aggregation (P. A. van Zwieten, Pathophysiological Relevance of Serotonin Journal of Cardiovascular Pharmacology, 10 (Suppl.3): S19-S25, 1987). Accordingly, it has been considered that a serotonin antagonist capable of selectively inhibiting serotonin activities such as platelet aggregation-accelerating activity and vasoconstriction activity, would inhibit the formation of thrombus and suppress the vasoconstriction, and therefore, would be useful for prophylactic or therapeutic treatment of various circulation disorders.

The following compounds are known to be useful as a serotonin antagonist:

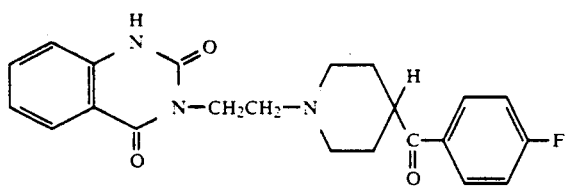

(3-[2-[4-(4-Fluorobenzoyl)-1-piperidinyl]ethyl]-2,4-(1H,3H)-quinazolindione (general name: Ketanserin)).

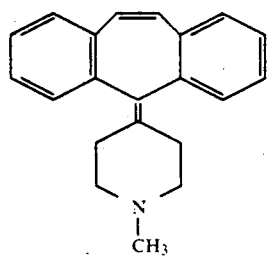

(4-(5H-Dibenzo[a,d]cyclohepten-5-ylidene)-1-methylpiperidine (general name: Cyproheptadine)).

The inventors of the present invention have found that aminoalkoxybibenzyls of the formula (I):

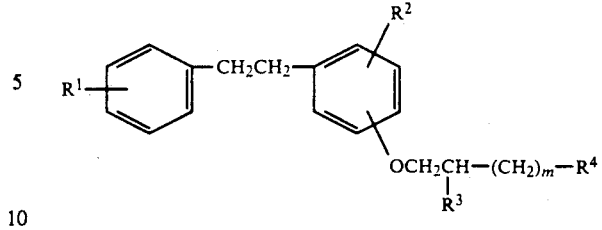

wherein:
R$^1$ is hydrogen, halo, C$_1$-C$_5$ alkoxy or C$_2$-C$_6$ dialkyl
R$^2$ is hydrogen, halo or C$_1$-C$_5$ alkoxy;
R$^3$ is hydrogen, hydroxy, —O—(CH$_2$)$_n$—COOH or —O—CO—(CH$_2$)$_1$—COOH, wherein n is an integer of 1-5, and l is an integer of 1-3;
R$^4$ is

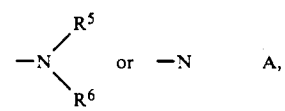

wherein R$^5$ and R$^6$ are each independently hydrogen or C$_1$-C$_8$ alkyl, and A is C$_3$-C$_5$ alkylene or C$_3$-C$_5$ alkylene substituted with carboxy; and
m is an integer of 0-5,
or a pharmaceutically acceptable salt thereof are useful as a serotonin antagonist.

Accordingly, one aspect of the present invention is to provide a method of suppressing vasoconstriction in a warm-blooded animal which comprises administering to said warm-blooded animal an effective amount of a serotonin-antagonist compound (I) to suppress vasoconstriction. Another aspect of the present invention is to provide the use of a compound (I) for the preparation of a pharmaceutical composition useful as a serotonin antagonist.

The compounds of the formula (I) are entirely different from the above-mentioned known serotonin antagonists in their chemical structures. However, the compounds (I) are very useful for improving various microcirculation disorders caused by thrombogenesis or vasoconstriction found in disorders of cerebral or peripheral blood flow, ischemic heart disease, and the like.

In the formula (I), specific examples of R$^1$ are hydrogen, halo such as chloro or fluoro, C$_1$-C$_5$ alkoxy such as methoxy, ethoxy or butoxy, or C$_2$-C$_6$ dialkylamino such as dimethylamino, diethylamino or methylethylamino; specific examples of R$^2$ are hydrogen, halo such as chloro or fluoro or C$_1$-C$_5$ alkoxy such as methoxy, ethoxy or butoxy; specific examples of R$^3$ are hydrogen, hydroxy, —O—(CH$_2$)$_n$—COOH (n is an integer of 1-5) such as —O—(CH$_2$)$_2$—COOH or —O—(CH$_2$)$_3$—COOH, or —O—CO—(CH$_2$)$_1$—COOH (l is an integer of 1-3) such as or —O—CO—(CH$_2$)$_2$—COOH or —O—(CH$_2$)$_3$—COOH: specific examples of R$^4$ are

(R$^5$ and R$^6$ are independently hydrogen or C$_1$-C$_8$ alkyl such as methyl, butyl, hexyl or heptyl) such as amino, methylamino, ethylamino, butylamino, hexylamino, heptylamino, dimethylamino, diethylamino or methylethylamino, or

(A is $C_3$-$C_5$ alkylene or $C_3$-$C_5$ alkylene substituted with carboxy) such as

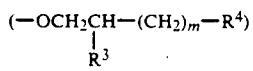

Preferred compounds (I) of the invention are those wherein aminoalkoxy $$(-OCH_2CH-(CH_2)_m-R^4)$$
$$\quad\quad\quad |$$
$$\quad\quad\quad R^3$$

is substituted at the 2 position of the phenyl ring; $R^1$ is hydrogen, $C_1$-$C_5$ alkoxy or $C_2$-$C_6$ dialkylamino; $R^2$ is hydrogen; $R^4$ is

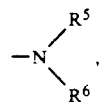

where at least either of $R^5$ or $R^6$ is $C_1$-$C_8$ alkyl, or $$-N\quad A$$

(A is methylene); m is an integer of 0–2.

The invention also includes pharmaceutically acceptable acid addition salts of the compounds defined by the above formula (I). Acids commonly employed to form such acid addition salts include hydrochloric, hydrobromic, sulfuric, phosphoric, nitric, acetic, succinic, adipic, propionic, tartaric, maleic, oxalic, citric, benzoic, toluensulfonic, and methanesulfonic acids, and the like.

The aminoalkoxybibenzyl compounds (I) used in the present invention are known as previously stated and can be easily prepared according to the process described in Japanese Patent Publication (Kokoku) No. 13427/1988.

By virtue of the serotonin inhibitory activity as demonstrated in the Example, the compounds of the invention can be employed in the treatment and prophylaxis of various circulatory disorders.

The compounds of the invention, strong serotonin antagonists, can be administered by any routes, orally or parenteraly, for example, via subcutaneous, intravenous, intramuscular or intraperitoneal injection.

The particular dose of the compound (I) to be administered to patients is determined by particular surrounding circumstances including age, physical conditions, or body weight of a patient to be treated, frequency of administration, and extent of the therapeutical effect to be expected. The dose will also vary if additional different treatment is conducted simultaneously.

A typical daily dose of the compound of the invention will range from about 0.5 mg/kg to about 50 mg/kg, and preferably, about 1 mg/kg to about 30 mg/kg. The daily dose can be administered in a single dose or in multiple doses.

The compounds of the invention are formulated in tablets, capsules, powders, solutions, elixirs for oral administration, and sterile injectable solutions or suspensions for parenteral administration. The pharmaceutical formulation of the present invention may contain nontoxic, solid or liquid, pharmaceutically acceptable carriers.

One of typical formulations of the invention is a hard or soft gelatin capsule. The formulations can also be in the form of tablets or sterile packaged powders containing an active compound together with or without adjuncts.

Capsules, tablets or powders generally contain about 5–95%, preferably about 25–90%, by weight of active compound(s) of the invention. It is preferred that the formulations are prepared in a unit dosage form so that each unit contain from about 5 to about 500 mg, preferably about 25 to 250 mg, of the active compound.

Specific examples of liquid carriers include sterile water, petroleum, and synthetic or natural oils from plant or animal sources, for example, peanut, soybean, mineral, or sesame oil. Preferred liquid carriers include physiological saline, an aqueous solution of dextrol or sucrose analog, and glycols such as ethylene glycol, propylene glycol, or polyethylene glycol. Injectable solutions prepared using physiological saline may contain from about 0.5 to about 20% by weight, preferably, about 1 to about 10% by weight of an active ingredient.

When the formulation is in the form of a solution for oral administration, it can be a suspension or a syrup containing from about 0.5 to about 10% by weight of an active ingredient together with liquid excipients, such as flavors, syrups, pharmaceutical micelles.

The following Example is illustrative only and is not intended to limit the scope of the invention in any respect.

EXAMPLE

Serotonin antagonistic activity of the compounds of the invention was evaluated according to receptor-binding test and inhibition test against serotonin-induced constriction of caudal artery in rats.

(1) Receptor-binding Test
(a) Preparation of Receptor

Wistar strain male rats (300–500 g) were killed by decapitation. Cerebral cortex was removed, homogenized in 50 mM Tris-HCl buffer, pH 7.4, and centrifuged at 50,000×g for 20 min at 4° C. After washing precipitates with the same buffer, the resultant nucleus-microsome-containing fraction (=receptor) was stored at −80° C. until use.

(b) Assay

The receptor obtained above (0.5 ml, equivalent to 5 mg of tissue) was incubated at 37° C. for 30 min in 0.4 ml of the above-mentioned buffer containing 0.1 ml of $^3$H-Ketanserin tracer (77 Ci/mmol; a final concentration of 1 nM) in the final volume of 1.0 ml. The reaction mixture was filtered under vacuum through a GF/B glass filter (Whatman). After washing the filter with the buffer, radio activity bound to filter was measured by a liquid scintilation spectrophotometer (Aloka, LSC-900) to obtain the total binding activity of the tracer.

Non-specific binding activity of the tracer, i.e., the binding activity of the tracer to materials other than the receptor, was evaluated using the same assay system except for that serotonin was added to the reaction mixture to the final concentration of 1 mM in order to block the binding of the tracer to the receptor. The specific binding activity of the tracer to the receptor was determined by subtracting the non-specific binding activity from the total binding activity.

(c) $IC_{50}$ (concentration of a test compound requisite for producing a 50% inhibition)

Concentration (ng/ml) of compounds of the invention (serotonin antagonist) which produces a 50% inhibition of specific binding of the tracer to the receptor was determined as follows.

The assay system and procedure as described in (b) were employed except for that amitriphtyline hydrochloride as a control or a compound of the invention was added to the assay system with various concentrations of from $10^{-1}$ to $10^{-5}$ ng/ml. The specific binding activity was determined at each concentration, and a dose-response curve was prepared. A concentration of the compound in ng/ml required for producing 50% inhibition of specific binding of the tracer to the receptor ($IC_{50}$) was determined on the basis of the dose-response curve. The test results are set forth below in Table 1.

(2) Inhibition Test against Serotonin-induced Constriction of Caudal Artery in Rats Wistar strain male rats (300–500 g) were sacrificed by striking the animals at the occiput. Caudal artery was removed and spiral strip was prepared according to the procedure of J. M. van Nueten, The Journal of Pharmacology and Experimental Therapeutics 218(1): 217-230 (1981).

The spirit strip was ligated at both ends with cotton thread and placed in a magnus tube containing 10 ml of Krebs-Henselite solution (37° C., bubbled with a mixture of 95% $O_2$ and 5% $CO_2$). One end of the thread was connected to Isometric Transducer (Nihon Koden-kogyo Kikai). Isometric contraction was measured using Isometric Amplifier (Nihon Koden-kogyo Kikai) under a tension of 0.5 g.

The control contruction by cumulatively added serotonin(final concentration: $10^{-9}$—$10^{-5}$M) was measured and then the control $ED_{50}$ value of serotonin was determined. Subsequently, the strip was washed three times with Krebs-Henselite solution and a compound of the invention was added at a suitable concentration (final concentration: $10^{-8}$, $10^{-7}$, $10^{-6}$, or $10^{-5}$M). Two minutes later, serotonin was cumulatively added at concentrations from $10^{-9}$ to $10^{-5}$ or $10^{-3}$M, and the $ED_{50}$ value in the test group was determined.

$ED_{50}$ values were calculated by "Probit Analysis". In Probit Analysis, an intercept, slope and spontaneous (threshold) reaction ratio of the curve obtained by biological analysis can be calculated according to the following "Probit equation" with highest reliability:

$$\Phi^{-1}\left(\frac{y-c}{1-c}\right) + 5 = a + bx$$

$\Phi$: the cumulative distributing relationships of standard normal distribution.

x: average dose (concentration of serotonin)

y: probability of reaction (contractility rate of vascular smooth muscle)

a, b, c: parameter; a, b>0, 1>c>0.

Inhibition constant (Ki) for each compound was determined according to the following equation:

$$Ki = \frac{[\text{concentration of compound to be tested}]}{\frac{ED_{50} \text{ (test group)}}{ED_{50} \text{ (control group)}} - 1}$$

The results are summarized in Table 1 below. In Table 1, decrease of $IC_{50}$ and Ki values of a test compound indicates increase of antagonistic effect of the compound.

As can be seen from the table, the compounds (I) of the present invention are useful as a serotonin antagonist which inhibits the formation of thrombus and suppresses vasoconstriction. Accordingly, the compounds (I) can be used for improving various microcirculation disorders caused by thrombogenesis or vasoconstriction found in disorders of cerebral or peripheral blood flow, ischemic heart disease, and the like.

The following formulation examples are illustrative only and are not intended to limit the scope of the invention in any way.

Formulation 1

Hard gelatin capsules are prepared using the following ingredients:

| | Quantity (mg/capsule) |
|---|---|
| Compound No. 1 (in Table 1) | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/tablet) |
|---|---|
| Compound No. 2 (in Table 1) | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

TABLE 1

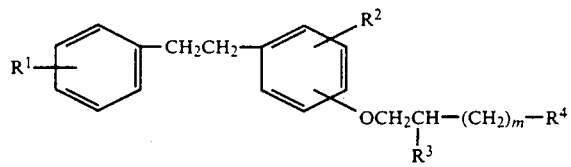

| Compound No. | R¹ | R² | position of aminoalkoxy | R³ | m | R⁴ | IC$_{50}$ (nM) | Ki (nM) |
|---|---|---|---|---|---|---|---|---|
| 1 | H | H | 2 | H | 0 | N(CH$_3$)$_2$ | 96.2 | 6.33 |
| 2 | H | H | 2 | H | 1 | N(CH$_3$)$_2$ | 33.8 | 4.55 |
| 3 | H | H | 2 | H | 2 | N(CH$_3$)$_2$ | 115.4 | 9.78 |
| 4 | H | H | 2 | H | 3 | N(CH$_3$)$_2$ | 377.0 | 37.6 |
| 5 | H | H | 2 | H | 4 | N(CH$_3$)$_2$ | 152.4 | 74.9 |
| 6 | H | H | 2 | H | 2 | NHCH$_3$ | 156.5 | 70.6 |
| 7 | H | H | 2 | H | 2 | NH$_2$ | 504.1 | 280 |
| 8 | H | H | 2 | H | 2 | 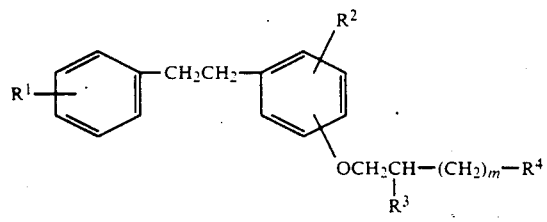 | 974.6 | 67.6 |
| 9. | H | H | 2 | H | 2 | 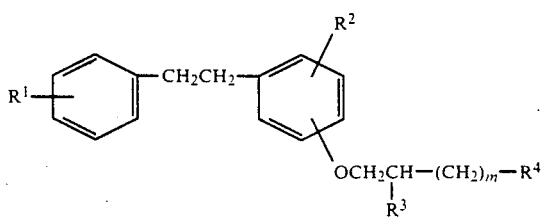 | 4479.0 | 198 |
| 10 | H | H | 3 | H | 2 | N(CH$_3$)$_2$ | 3328.3 | 517 |
| 11 | H | H | 4 | H | 2 | N(CH$_3$)$_2$ | 1976.0 | 416 |
| 12 | 3-OCH$_3$ | H | 2 | H | 2 | N(CH$_3$)$_2$ | 62.2 | 13.1 |
| 13 | 4-N(CH$_3$)$_2$ | H | 2 | H | 1 | N(CH$_3$)$_2$ | 53.6 | 23.3 |
| 14 | 3-OCH$_3$ | H | 2 | OCO(CH$_2$)$_2$COOH | 1 | N(CH$_3$)$_2$ | 51.3 | 17.8 |
| 15 | 3-OCH$_3$ | H | 2 | OH | 1 | N(CH$_3$)$_2$ | 12.5 | 1.16 |
| 16 | 3-OCH$_3$ | H | 2 | O(CH$_2$)$_2$COOH | 1 | N(CH$_3$)$_2$ | 68.6 | 1.05 |
| 17 | 3-F | H | 2 | OCO(CH$_2$)$_2$COOH | 1 | N(CH$_3$)$_2$ | 132.5 | 41.3 |
| 18 | H | H | 2 | OH | 1 | N(CH$_3$)$_2$ | 54.8 | 13.9 |
| 19 | 3-Cl | H | 2 | H | 2 | N(CH$_3$)$_2$ | 812.5 | 13.5 |
| 20 | H | 5-Cl | 2 | H | 2 | N(CH$_3$)$_2$ | 881.4 | 25.7 |
| 21 | H | 3-OCH$_3$ | 2 | H | 2 | N(CH$_3$)$_2$ | 563.7 | 85.7 |

What is claimed is:

1. A method of suppressing vasoconstriction in a warm-blooded animal which comprises administering to said warm-blooded animal an effective amount of a serotonin antagonist compound of the formula (I):

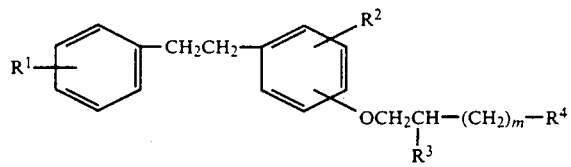

wherein:
R¹ is hydrogen, halo, C$_1$-C$_5$ alkoxy or C$_2$-C$_6$ dialkyl amino;
R² is hydrogen, halo or C$_1$-C$_5$ alkoxy;
R³ is hydrogen, hydroxy, —O—(CH$_2$)$_n$—COOH or —O—CO—(CH$_2$)$_l$—COOH, wherein n is an integer of 1–5, and l is an integer of 1–3; R³ is

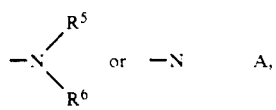

wherein R⁵ and R⁶ are each independently hydrogen or C$_1$-C$_8$ alkyl, and A is C$_3$-C$_5$ alkylene or C$_3$-C$_5$ alkylene substituted with carboxyl; and
m is an integer of 0–5,
or pharmaceutically acceptable salt thereof.

2. A method of suppressing vasoconstriction in a warm-blooded animal which comprises administering to said warm-blooded animal an effective amount of a serotonin antagonist compound of the formula (I):

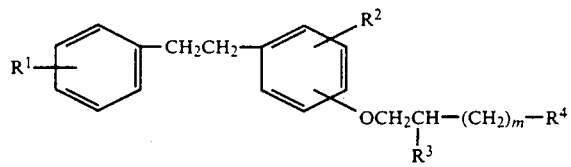

wherein:
R¹ is hydrogen, halo, C$_1$-C$_5$ or C$_2$-C$_6$ dialkyl amino;
R² is hydrogen, halo or C$_1$-C$_5$ alkoxy;
R³ is —O—(CH$_2$)$_n$—COOH or —O—CO—(CH$_2$)$_l$—COOH, wherein n is an integer of 1–5, and l is an integer of 1–3;
R⁴ is

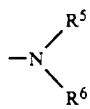
wherein R⁵ and R⁶ are each independently hydrogen or $C_{1-C_8}$ alkyl; and
m is an integer of 0–5,
or a pharmaceutically acceptable salt thereof.
3. The method of claim 2, wherein the compound has the formula
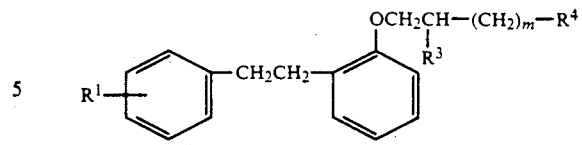
wherein
R¹, R³ and R⁴ are defined as in claim 3, and
m is 0–2.
4. 2[{3-dimethylamino-2)3-carboxypropionyloxy)} propoxy]3'-methoxybibenzyl.